United States Patent [19]
Ailinger et al.

[11] Patent Number: 5,329,887
[45] Date of Patent: Jul. 19, 1994

[54] ENDOSCOPE CONTROL ASSEMBLY WITH REMOVABLE CONTROL KNOB/BRAKE ASSEMBLY

[75] Inventors: Robert E. Ailinger, Norwood; Robert J. Herrington, Holland, both of Mass.

[73] Assignee: Vision Sciences, Incorporated, Natick, Mass.

[21] Appl. No.: 862,810

[22] Filed: Apr. 3, 1992

[51] Int. Cl.⁵ ............................................. A61B 1/00
[52] U.S. Cl. ......................................... 128/4; 403/328
[58] Field of Search ............... 128/4, 6, 7, 8, 11; 138/120; 403/358, 359, 326, 328; 116/DIG. 31; 292/348, 352, 353, 179

[56] References Cited

U.S. PATENT DOCUMENTS

| | | | |
|---|---|---|---|
| 1,287,463 | 12/1918 | Schwitzer | 403/326 |
| 4,078,555 | 3/1978 | Takahashi | 128/4 |
| 4,370,773 | 2/1983 | Hadary | 403/328 X |
| 4,461,282 | 7/1984 | Ouchi et al. | 128/4 |
| 4,504,167 | 3/1985 | Nakanishi | 403/328 X |
| 4,522,196 | 6/1985 | Cunningham et al. | 128/6 X |
| 4,617,914 | 10/1986 | Ueda | 128/4 |
| 4,742,816 | 5/1988 | Suzuki et al. | 128/4 |
| 4,825,850 | 5/1989 | Opie et al. | |
| 5,007,406 | 4/1991 | Takahashi et al. | 128/4 |
| 5,127,764 | 7/1992 | Baer | 403/326 X |
| 5,168,863 | 12/1992 | Kurtzer | 128/4 |

Primary Examiner—Richard J. Apley
Assistant Examiner—Karen A. Jalbert
Attorney, Agent, or Firm—Seed and Berry

[57] ABSTRACT

A removable control knob/brake assembly for an endoscope having a handle and an insertion tube. The assembly is intended to be used with endoscopes which use protective bags or sheaths to isolate the insertion tube and the remainder of the handle from the internal environment of a patient. The control knob/brake assembly is not otherwise protected so, after being used, it must be removed for cleaning. A simple push button release mechanism is provided to easily remove the assembly from the handle. Retaining screws and a retaining clip are provided to prevent the control knob/brake assembly from coming apart when the assembly is removed from the handle. To attach the assembly to the handle, it merely is pushed on the handle.

18 Claims, 4 Drawing Sheets

ENDOSCOPE CONTROL ASSEMBLY WITH REMOVABLE CONTROL KNOB/BRAKE ASSEMBLY

1. Field of the Invention

This invention relates to the field of endoscopy, and more particularly, to partially detachable control apparatus for use with a system for isolating an endoscope from viruses and bacteria during use.

2. Background of the Invention

The use of endoscopes for diagnostic and therapeutic indications is rapidly expanding. To improve performance, endoscopes have been optimized to best accomplish their purpose. Therefore, there are upper endoscopes for examination of the esophagus, stomach and duodenum; colonoscopes for examining the colon; angioscopes for examining blood vessels; bronchoscopes for examining the bronchi; laparoscopes for examining the peritoneal cavity; and arthroscopes for examining joint spaces. The discussion which follows will apply to all of these types of endoscopes.

Instruments to examine the rectum and sigmoid colon, known as flexible sigmoidoscopes are good examples of the usefulness of endoscopic technology. These devices are expensive, and they are used in a contaminated environment for a procedure which is brief (5–10 minutes) and where problems of cleaning time and contamination are important factors. There has been a large increase in the use of the "flexible sigmoidoscope" for use in screening symptomatic and asymptomatic patients for colon and rectal cancer. Ideally, flexible sigmoidoscopes must be used rapidly and inexpensively in order to maintain the cost of such screening at acceptable levels. Typically, a clinic would like to perform five sigmoidoscope examinations each hour. A significant problem with making such examinations quick and inexpensive is the time necessary for adequately cleaning the device.

In the health care field, the problems of contaminated instruments transmitting disease from one patient to the next have generally been solved by making such instruments disposable. However, until recently, this approach has not been through possible in the field of endoscopy because endoscopes are very expensive instruments. Moreover, it has not been thought possible to isolate the endoscope from the patient or the external environment because the endoscope itself has channels inside it that are used as a conduit for body fluids and tissues, such as, for example, in taking biopsies. The only method currently available to actually sterilize an endoscope is to use gas sterilization with ethylene oxide gas. However, there are several disadvantages in using this procedure. The procedure is very slow (up to 24 hours) during which the endoscope cannot be used. Also, the gas affects the plastic of the endoscope and may limit its life span. Finally, the gas is toxic, and, therefore, great care must be taken to ensure that no residue remains that might cause patient or staff, irritation or allergic reaction during contact with the endoscope.

An approach to the problem of endoscope contamination is described in U.S. Pat. No. 4,646,722. This approach involves the use of an endoscope sheath having a flexible tube surrounding the elongated core of an endoscope. After use, the sheath is removed and disposed of, leaving the endoscope free of contamination resulting from the endoscopic procedure.

The sheath preferably includes an air channel, a water channel, and a suction/biopsy channel. All of these channels are discarded along with the sheath. However, there is still a problem with the control handle of the endoscope. The way endoscopes are used clinically is that the control handle of endoscope. The way endoscopes are used clinically is that the control handle of the instrument is held in the endoscopist's left hand. The right hand is usually placed on the endoscope's shaft to advance the instrument into the patient and to pull the instrument out of the patient. This results in contamination of the right hand with patient secretions including blood, mucus, stool, and tissue. This contamination occurs during every endoscopic procedure. The endoscopist wears gloves to protect his or her hand. However, during the procedure, the endoscopist frequently must reach up with his or her right hand and move the knobs of the endoscope control apparatus. These knobs control up/down and left/right movement of the controllable tip bending section of the endoscope. Although it is possible to control these knobs somewhat with the left hand, it is often essential to reach up with the right hand to assist with a complex control movement. This results in the immediate contamination of the endoscope control apparatus. Often the body of the control handle is contaminated as well as the control assembly handle.

U.S. Pat. No. 4,825,850 addresses this contamination of the control body and control assembly. The patent described the use of a fluid-impermeable bag to cover the control handle, thereby preventing contamination. The control knobs could be placed inside the bag so that they are manipulated through the bag. However, placing the control knobs inside the bag makes it very difficult to manipulate them, particularly when they must be rotated in opposite directions. Therefore it is desirable to place the control knobs outside of the bag. Since the knobs are not protected by the bag, it is desirable to make them removable so that they can be sterilized or discarded and replaced.

The '850 patent provides a control assembly with removable control knobs. However, only a portion of the control assembly is removable. The entire braking mechanism for one of the control knobs remains affixed to the control handle. The '850 patent discloses the use of a release button to mount the removable portion of the control assembly to the body of the handle. The release button must be pressed both to disengage the removable portion from the handle and to mount the removable portion to the handle. This requirement of pressing the release button when mounting the removable portion adds unnecessary complication to the endoscope preparation.

The present invention builds upon the concept disclosed in the '850 patent and provides an improved removable control knob apparatus.

SUMMARY OF THE INVENTION

It is an object of the invention to provide an endoscope having easily removable control knobs so that the knobs can be sterilized or discarded after use.

It is a further object of the invention to provide a control apparatus for an endoscope that allows a braking system to be removed with the control knobs.

It is a further object of the invention to provide a control knob apparatus that is relatively simple to build and repair.

These and other objects of the invention are provided by a combined control knob/brake apparatus that allows the braking assemblies to be removed along with the control knobs. The apparatus is provided with a push button slide that engages the shaft leading to the control handle when the endoscope is being used, but can easily be disengaged by pushing the button. The apparatus is mounted to the endoscope handle simply by pushing it on the handle without needing to activate the push button slide. To provide more stability to the apparatus, set screws, a washer and a spring clip have been strategically located within the apparatus.

DETAILED DESCRIPTION OF THE INVENTION

Figure 1:
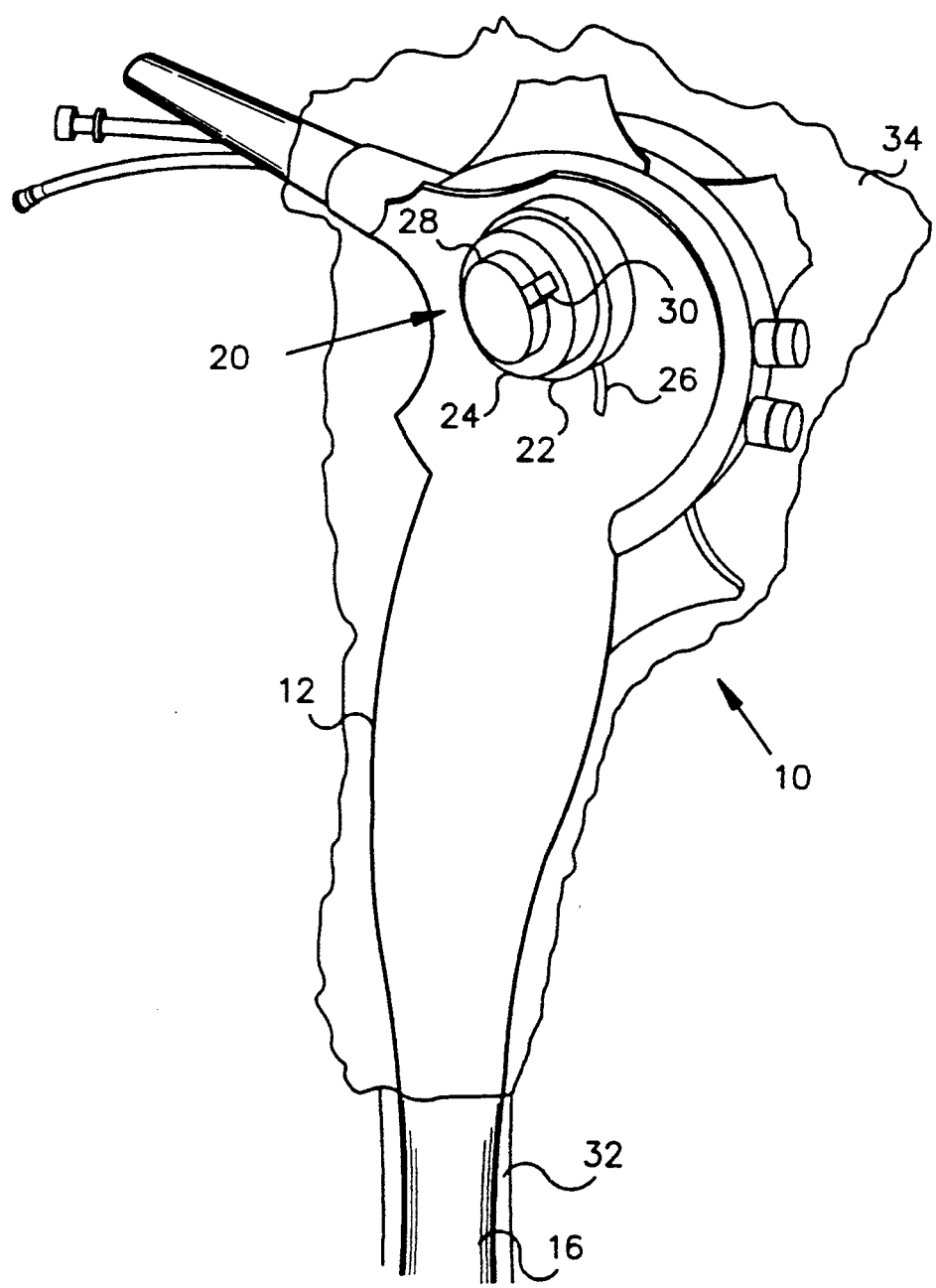
FIG. 1 is an isometric view of an endoscope handle having a removable control knob/brake assembly.

A conventional endoscope 10 includes a handle 12 and an insertion tube 16 as shown in FIG. 1. The handle 12 includes a control assembly 20 that enables a user to manipulate the angular orientation of the distal end of the insertion tube 12. The insertion tube 16 is manipulated in the up and down direction by rotating an up/down ("U/D") control knob 22 in opposite directions and in the left and right directions by manipulating a left/right ("L/R") control knob 24. As explained in greater detail below, the control knobs 22, 24 drive respective pulleys, each of which retract and pay out a pair of complementary control cables (not shown) extending through the insertion tube 16 to its distal end. The control knobs 22, 24 can be frictionally locked through respective braking mechanisms, as also described in greater detail below. A U/D brake activating lever 26 is used to control the braking mechanism that locks U/D control knob 22 while L/R brake activating knob 28 controls the braking mechanism that locks L/R control knob 24. In contrast to prior art braking mechanisms, both braking mechanisms of the present invention are removable with the control knobs 22, 24. Removal of the control knobs 22, 24 and braking mechanism is accomplished simply by pressing release button 30.

The inventive endoscope 10 is most advantageously used with a sheath 32 surrounding the insertion tube 16 to prevent contamination of the insertion tube 16. The endoscope 10 also is intended to be used with a protective bag 34 that surrounds the endoscope handle 12 except for control assembly 20 to prevent contamination of the handle 12. The bag 34 preferably mates with the protective sheath 32 to prevent contamination of the endoscope 10 at the junction between the bag 34 and sheath 32.

At the conclusion of an endoscopic procedure, the control knobs 22, 24 and accompanying braking mechanisms are removed from the handle 12 and sterilized or discarded. The handle 12 is then removed from the bag 34 and the insertion tube 16 is removed from the sheath 32. As a result, the only parts of the endoscope 10 that become contaminated are the control knobs 22, 24, the brake actuating lever/knob 26, 28, and the release button 30.

Figure 2:
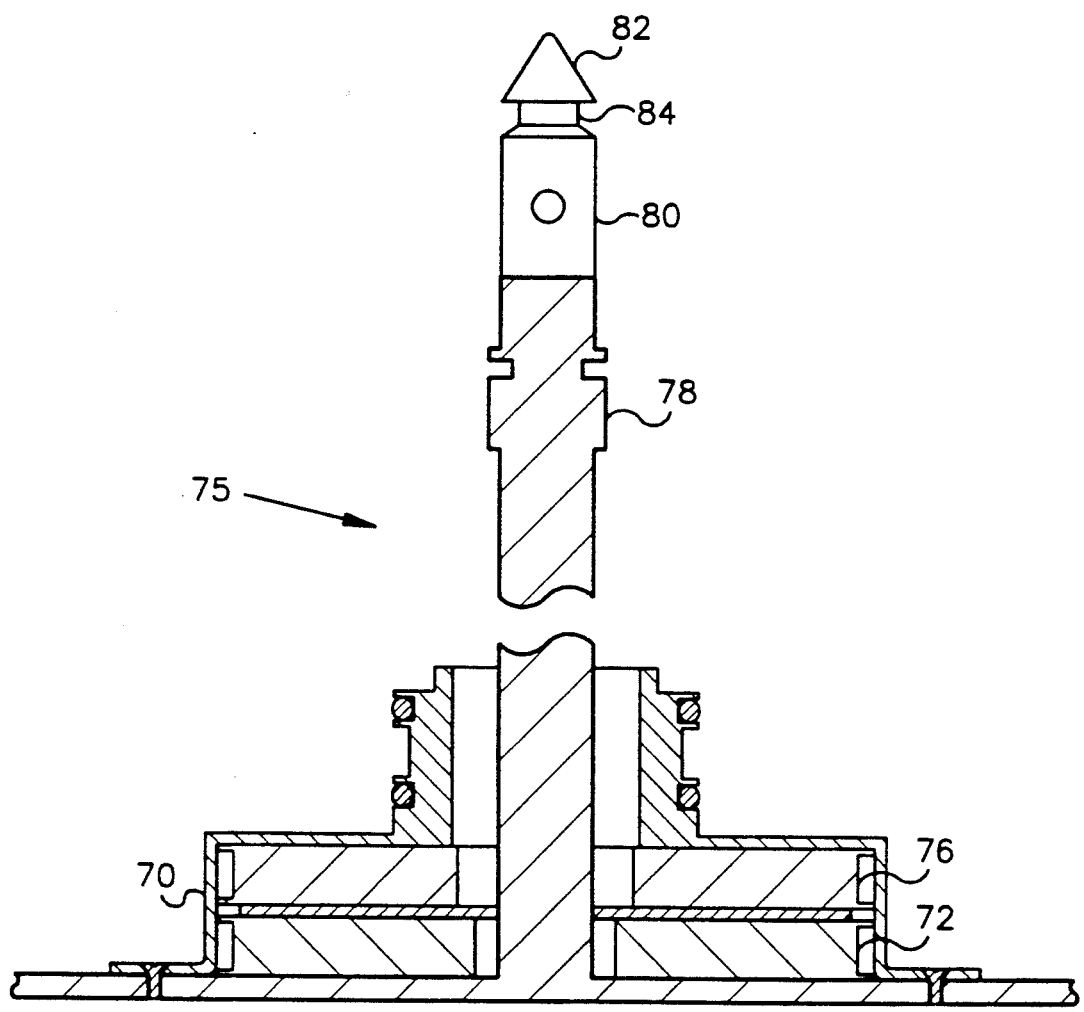
FIG. 2 is a longitudinal sectional view of a support assembly of an endoscope insertion tube control assembly.
Figure 3:
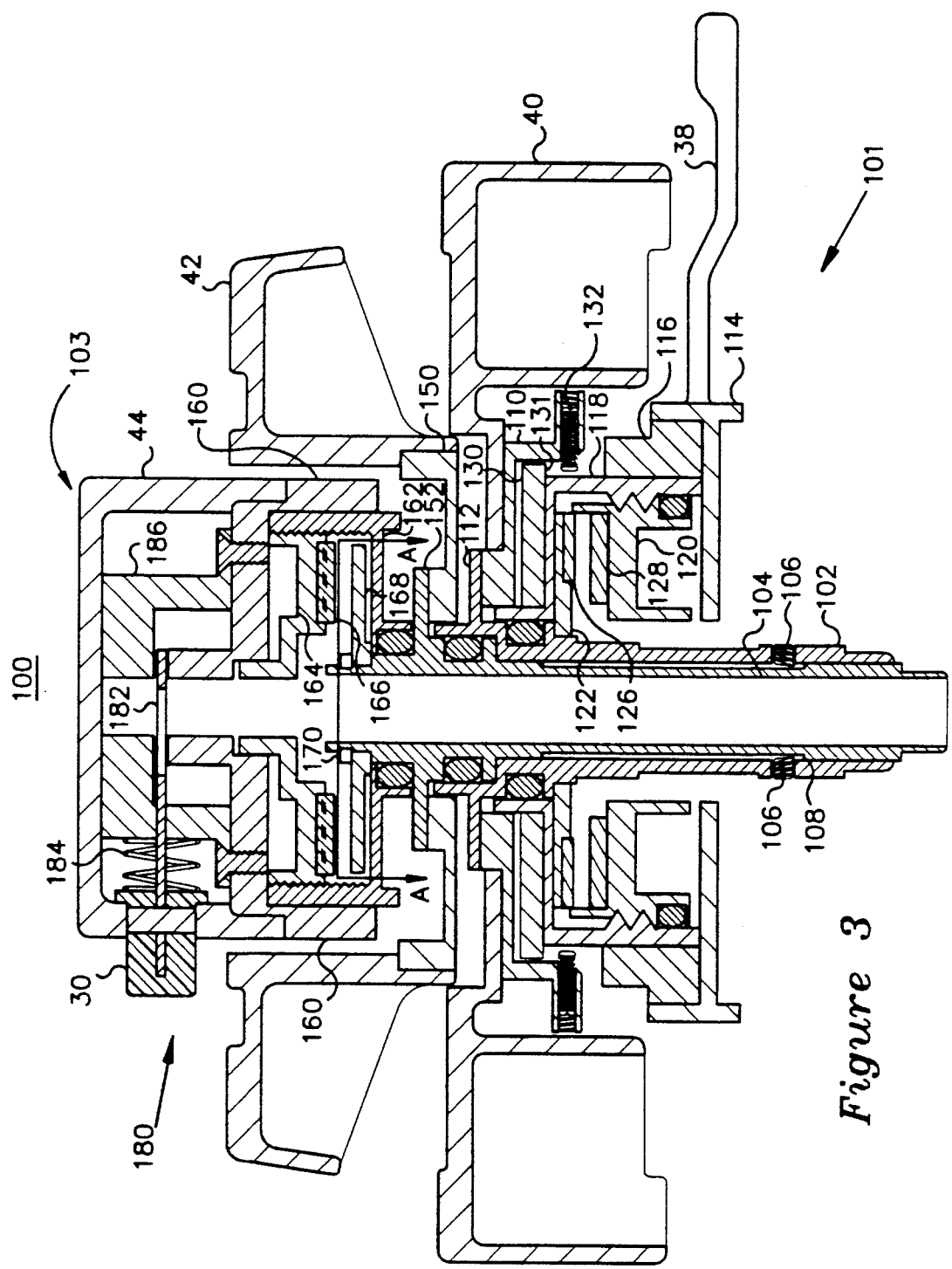
FIG. 3 is a longitudinal sectional view of a removable control knob/brake assembly of an endoscope insertion tube control assembly.

The endoscope control assembly 20 includes a support assembly 75 (FIG. 2) and a detachable control knob/brake assembly 100 (FIG. 3). With reference to FIG. 2, the support assembly 75 includes a cylindrical housing 70 mounted within the handle 12. The housing 70 encloses an L/R pulley or drum 72 on which right-/left control cables (not shown) are wound and a pulley or drum 76 on which up/down control cables (not shown) are wound. The left/right control cables are connected to diametrically opposite portions of the insertion tube 16 at the distal ends to control the upward and downward movement of the distal end of the insertion tube 16 responsive to the rotation of the pulley 72 in the opposite directions. Similarly, the up/down control cables are connected to diametrically opposite portions of the distal end of the insertion tube 16 so that the distal end of the insertion tube 16 moves down and up responsive to rotation of the pulley 76 in the opposite directions.

An elongated shaft support 78 extends concentrically through the pulleys and outward from the handle. The distal end of the shaft support, i.e., the end furthest from the handle, forms a release pin 80 to be engaged with the control knob/brake assembly 100. The release pin has a tapered head 82 so that it is guided into engagement with a control knob/brake assembly engagement mechanism described in detail below. A concentric groove 84 immediately below the tapered head acts as a receptacle for the engagement mechanism, thereby locking the engagement mechanism under the tapered head as discussed more fully below.

FIG. 3 shows the control knob/brake assembly portion 100 of the endoscope insertion tube control assembly 20 (FIG. 1). The control knob/brake assembly 100 includes an L/R control shaft 104 positioned concentrically inside U/D control shaft 102. When the control knob/brake assembly 100 is fully in place on the endoscope handle 12, the shaft support 78 mates with the control shafts 102, 104. When fully in place, the L/R control shaft 104 is coupled to the L/R drum 72 such that rotation of the control shaft rotates the drum, which in turn causes the insertion tube to move to the left or to the right. Similarly, the U/D control shaft 102 is coupled to the U/D drum 76 such that rotation of the control shaft rotates the drum and causes the insertion tube to move up or down.

Shaft retaining screws 106 extend through the U/D control shaft 102 and into a space between the control shafts. A shaft retaining ridge 108 formed on the exterior of the L/R control shaft 104 cooperates with the shaft retaining screws 106 to prevent downward motion of the U/D control shaft 102 with respect to the L/R control shaft 104. The shaft retaining screws 106 extend only so far into the space between the control shafts so as to be able to cooperate with the retaining ridge 108 without disabling rotational motion of the control shafts with respect to each other.

The U/D control shaft 102 is keyed to the U/D control knob 40 via a U/D coupling member 110 so that the shaft 102 and knob 40 rotate together. U/D coupling member 110 is connected to a U/D shaft flange 112 extending from the U/D control shaft 102. U/D coupling member 110 is connected to the U/D control knob 40 such that rotation of the control knob 40 rotates the coupling member 110 and in turn rotates the U/D control shaft 102.

As discussed above, in contrast to the prior art endoscopes, the entire U/D braking assembly 101 is removable with the remainder of the control knob/brake assembly 100. The U/D braking assembly 101 includes a U/D brake actuating lever 38 which is secured to a brake coupling member 114 which in turn is coupled to brake ring 116. Brake ring 116 is secured to an internally threaded brake housing 118 such that turning of the brake actuating lever 38 causes the brake housing to rotate about the control shafts. The internal threads of the U/D brake housing 118 are keyed to external threads of a brake activating member 120 such that rotation of the brake housing causes the brake activating member to move away from the endoscope handle 12. Secured to the U/D control shaft 102 is a U/D brake pad support 122 having a U/D brake pad 126 affixed to its bottom face such that rotation of the control shaft 102 causes the brake pad support 122 and brake pad 126 to rotate. When the U/D brake activating member 120 moves away from the endoscope handle 12 by rotating the brake housing 118, it causes U/D brake plate 128 to move to contact U/D brake pad 126. Friction between the brake pad 126 and brake plate 128 prevents the brake pads and the U/D brake pad support 122 from rotating with respect to the brake plate 128. The rotational restraint of the U/D brake pad support 122 prevents rotation of the U/D control shaft 102 because of their secure connection together. Friction between the threads of the U/D brake activating member 120 and the threads of the U/D brake housing 118 ensure that rotational force on the U/D control shaft 102 will be insufficient to overcome the friction between the brake pad 126 and the brake plate 128. Turning the U/D brake actuating lever 38 in the opposite direction causes brake activating member 120 to move away from brake pad 126, thereby freeing the control shaft 102 for subsequent rotation.

To help prevent the U/D braking assembly 101 from being detached from the remainder of the control knob/brake assembly 100 a brake retaining washer 130 is positioned between the upper portion of the U/D brake housing 118 and the lower portion of the up/down coupling member 110. Brake retaining screws 132 extend through a lower portion of the U/D coupling member 110 and capture the outer edge 131 of the brake retaining washer 130. The brake retaining screws 132 extend only so far as to extend beneath the outer edge of the brake retaining washer 130, but not so far as to couple the rotation of the up/down coupling member 110 to the rotation of the up/down brake housing 118.

The L/R control shaft 104 is actuated similarly to that of the U/D control shaft 102. The control mechanism includes L/R control knob 42, which is secured to L/R coupling member 150 by conventional means. The coupling member 150, in turn, is secured to L/R shaft flange 152 extending from L/R control shaft 104. Turning L/R control knob 42 in either direction causes the L/R control shaft 104 to move in the same direction.

The left/right braking assembly 103 includes a L/R brake actuating knob 44 affixed to a L/R brake housing 160, which is secured to a L/R brake coupling member 162. An externally threaded brake activating member 164 having L/R brake pad 166 affixed to its bottom face mates with the internal threads of the L/R brake coupling member 162 such that rotation of the brake coupling member 162 causes the brake activating member 164 to move towards the endoscope handle 12. When the brake pad 166 moves toward the endoscope handle 12, it contacts L/R brake plate 168, which is affixed to the L/R control shaft 104. Friction between the brake pad 166 and the brake plate 168 prevents the L/R control shaft 104 from rotating. Friction between the threads of the L/R brake activating member 164 and the threads of the L/R brake coupling member 162 ensure that rotational force on the L/R control shaft 104 will be insufficient to overcome the friction between the brake pad 166 and the brake plate 168. A spring clip 170 is provided to engage the L/R control shaft 104 and the L/R brake plate 168 to prevent the L/R braking assembly from disengaging from the control shafts, as discussed more fully below.

Figure 4:
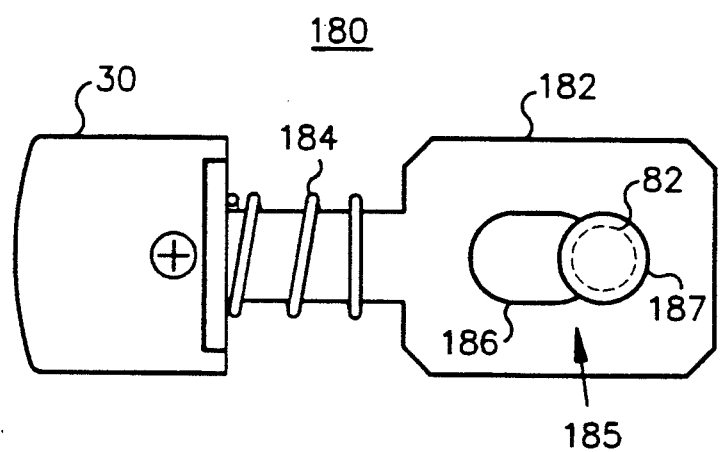
FIG. 4 is an elevational view of a fastening mechanism for a removable control knob/brake assembly.

In contrast to the prior art, the invention provides a simple one-touch engagement mechanism 180 that allows the control knob/brake assembly 100 to be mounted to the endoscope handle 12 without pressing a release button. As shown best in FIG. 4, the engagement mechanism 180 consists of release button 30 secured to a release slide 182 and outwardly biased by spring 184. When the control knob/brake assembly 100 is pushed onto the endoscope handle 12, the head 82 of the release pin 80 pushes through the release slide 182. The tapered head 82 moves the release slide 182 inwardly so as to push the release pin through the release slide. Once the head 82 is all of the way through the release slide, the spring 184 causes the release slide to engage groove 84 located beneath the head 82. The engagement mechanism 180 is supported by slide brace 186, which is affixed to L/R brake housing 160 by a pair of screws. The release slide 182 has an aperture 185 with a large circular end 186 extending to a smaller circular end 187. The head 82 of the release pin 80 extends through the large portion 186 of the aperture 185 which pulls the release slide inwardly as discussed above. Once the head 82 is completely through the large portion 186 of the aperture 185, the release slide is forced back by spring 184 to engage the groove 84 in the smaller portion 187 of the aperture. This simple mechanism allows the control knob/brake assembly 100 to be attached to the endoscope handle 12 simply by pushing it onto the handle. To remove the control knob/brake assembly 100 from the endoscope handle 12, a simple push of release button 30 causes the head 82 of release pin 80 to become disengaged from the smaller portion 187 of the release slide aperture 185. The control knob/brake assembly 100 can then be removed from the endoscope handle 12 simply by pulling it away and allowing the head 82 to escape through the large portion 186 of the release slide aperture 185.

Figure 5:
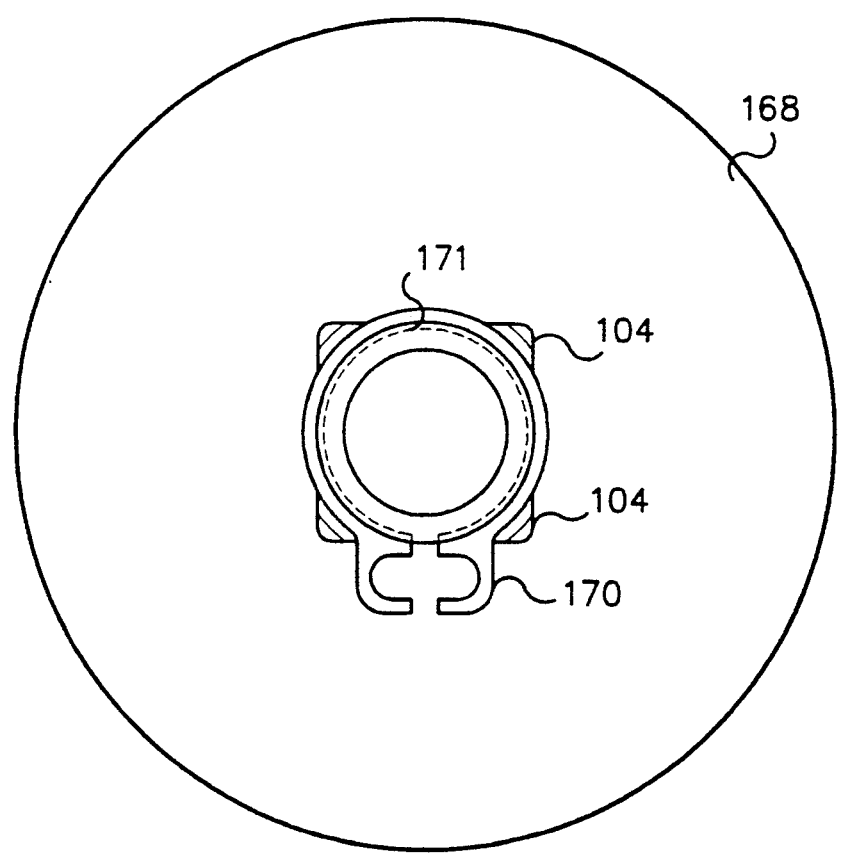
FIG. 5 is an elevational view of a spring clip used to prevent detachment of the braking mechanism from the control shaft.

FIG. 5 is a cross-sectional view taken along the line A—A in FIG. 3 of the coupling of the spring clip 170 to the L/R control shaft 104 and L/R brake plate 168. The inside diameter of the spring clip 170 is sized to be slightly smaller than the outside of the L/R control shaft 104. To couple the spring clip 170 to the L/R control shaft 104 one could rely on the clamping action caused by putting the smaller clip 170 on the larger shaft 104. However, preferably the L/R control shaft has a groove 171 into which spring clip 170 is engaged. The groove 171 is positioned at or slightly above the brake plate 168 so that the spring clip 170 engages the brake plate and prevents the L/R braking assembly 103 from disengaging from the control shafts.

It is apparent from an examination of FIG. 3 that the entire control knob/brake assembly 100 is removable as a unit. The only components of the control assembly 20 that remain on the handle of the endoscope are those comprising the support assembly 75 shown in FIG. 2. However, all of these components are shielded during use by the control knob/brake assembly 100 illustrated in FIG. 3. As a result, the protective bag 34, coupled with the removal and sterilization of the control and braking mechanism after each use, prevents contamination of the endoscope handle 12.

It will be appreciated that, although specific embodiments of the invention have been described herein for purposes of illustration, various modifications may be made without departing from the spirit and scope of the invention. Accordingly, the invention is not limited except as by the appended claims.

We claim:

1. An endoscope insertion tube control assembly for an endoscope having a handle and an elongated inserting tube extending from the handle to a distal end comprising:

an elongated support shaft projecting from the handle;

a removable first controlling means for controlling up/down movement of the distal end of the insertion tube;

removable second controlling means for controlling left/right movement of the distal end of the insertion tube;

removable braking means for braking up/down and left/right movement of the insertion tube, the braking means being coupled to the controlling means such that the braking means and the controlling means are removable as a unit, the braking means including:

a first braking mechanism, coupled to the first controlling means, for releasably restricting up/down movement of the insertion tube; and a first brake actuating means coupled to the first braking mechanism, for causing the first braking mechanism to restrict up/down movement of the insertion tube;

a second braking mechanism, coupled to the second controlling means, for releasably restricting left/right movement of the insertion tube; and a second brake actuating means coupled to the second braking mechanism, for causing the second braking mechanism to restrict left/right movement of the insertion tube; and fastening means for releasably securing the unit that includes the braking means and the controlling means to the support shaft.

2. The endoscope insertion tube control assembly of claim 1, wherein the elongated support has a distal end furthest from the handle and a transverse groove located near the distal end; and the fastening means comprises a spring loaded release slide having an aperture, the release slide being adapted to receive the end of the elongated support within the aperture and to releasably engage the transverse groove to secure the control means to the handle.

3. The endoscope insertion tube control assembly of claim 2 wherein the distal end of the support shaft forms a tapered head such that the tapered head causes the release slide to move to allow the head to be received by the slide release aperture and thereby allowing the release slide to releasably engage the transverse groove.

4. The endoscope insertion tube control assembly of claim 3 wherein the distal end of the support shaft forms a conical tapered head adjacent the transverse groove, the tapered head being positioned to extend into the release slide aperture, move the release slide, and force the release slide to compress a spring loading the release slide, thereby allowing the tapered head to extend through the release slide aperture to allow the release slide to releasably engage the transverse groove.

5. The endoscope insertion tube control assembly of claim 1 wherein the up/down and left/right braking means include means for adjusting, while the unit is secured to the control shaft, the braking force applied in braking the up/down and left/right movement of the insertion tube.

6. An endoscope insertion tube control assembly for an endoscope having a handle and an elongated insertion tube extending from the handle to a distal end, comprising:

an elongated support shaft projecting from the handle; and a removable control knob/brake assembly including:

a first control shaft adapted to control movement of the distal end of the insertion tube in a first plane;

a second control shaft adapted to control movement of the distal end of the insertion tube in a second plane, the second control shaft being concentrically positioned within the first control shaft and concentrically positioned around the support shaft;

a first pad of frictional braking material coupled to the first control shaft so that the first braking pad and first control shaft rotate together;

a first brake plate adjacent the first frictional pad;

a first brake actuating means for moving the first brake plate into frictional contact with the first braking pad in order to restrain rotation of the first brake pad and first control shaft;

a first control means coupled to the first control shaft for causing rotation of the first control shaft;

a second control means coupled to the second control shaft for causing rotation of the second control shaft;

a second brake plate coupled to the second control shaft so that the second brake plate and second control shaft rotate together;

a second pad of frictional braking material positioned adjacent the second brake plate;

a second brake actuating means for moving the second braking pad into frictional contact with the second brake plate in order to restrain rotation of the second brake plate and second control shaft; and fastening means for releasably securing the control knob/brake assembly to the elongated support shaft.

7. The endoscope insertion tube control assembly of claim 6 wherein the elongated support has a distal end furthest from the handle and a transverse groove located near the distal end; and the fastening means comprises a spring loaded release slide having an aperture, the release slide being adapted to receive the end of the elongated support within the aperture and to releasably engage the transverse groove to secure the control knob/brake assembly to the shaft support.

8. The endoscope insertion tube control assembly of claim 7 wherein the distal end of the support shaft forms a tapered head such that the tapered head causes the release slide to move to allow the head to be received by the slide release aperture and thereby allowing the release slide to releasably engage the transverse groove.

9. The endoscope insertion tube control assembly of claim 6, further comprising a clip positioned concentrically around the second control shaft so as to prevent detachment of the second brake plate from the second control shaft.

10. The endoscope insertion tube control assembly of claim 6 wherein the second control shaft includes a retaining ridge formed on its exterior, the insertion tube control assembly further comprising a plurality of shaft set screws extending transversely through the first control shaft, the set screws extending far enough into a space between the control shafts engage the retaining ridge and thereby stabilize axial movement between the control shafts when the control knob assembly is removed from the handle.

11. An endoscope insertion tube control assembly for an endoscope having a handle and an elongated insertion tube extending from the handle to a distal end, comprising:
   an elongated support shaft projecting from the handle; and
   a removable control knob/brake assembly comprising:
      a first control shaft adapted to control movement of the distal end of the insertion tube in a first plane;
      a second control shaft adapted to control movement of the distal end of the insertion tube in a second plane, the second control shaft being concentrically positioned within the first control shaft and concentrically positioned around the support shaft;
      a first pad of frictional braking material coupled to the first control shaft so that the first braking pad and first control shaft rotate together;
      a first brake plate adjacent the first frictional pad;
      a brake actuating lever secured to a first threaded coupling member;
      a first brake activating member, secured to the first brake plate, having threads mated to the first threaded coupling member such that rotation of the brake actuating lever causes the first brake activating member to move the first brake plate toward the first braking pad, thereby forcing the first brake plate against the braking pad in order to restrain rotation of the braking pad and the first control shaft;
      a first control knob coupled to the first control shaft by a first control coupling member such that rotation of the control knob causes rotation of the first control shaft;
      a second control knob coupled to the second control shaft such that rotation of the control knob causes rotation of the second control shaft;
      a second brake plate coupled to the second control shaft so that the second brake plate and second control shaft rotate together;
      a second pad of frictional braking material positioned adjacent the second brake plate;
      a brake actuating knob secured to a second threaded coupling member;
      a second brake actuating member, to which the second braking pad is secured, having threads mated to the first threaded coupling member such that rotation of the brake actuating knob causes the second brake actuating member to move the second braking pad toward the second brake plate, thereby forcing the second braking pad against the second brake plate in order to restrain rotation of the second braking plate and the second control shaft;
      a washer positioned between the first control coupling member and the first threaded coupling member; and
      a plurality of set screws extending from the first control coupling member such that when the control knob/brake assembly is removed from the support shaft the plurality of set screws engage the washer and prevent excessive axial movement of the first threaded coupling member relative to the first control member.

12. The endoscope insertion tube control assembly of claim 11, further comprising fastening means for releasably securing the control knob/brake assembly to the elongated support shaft.

13. The endoscope insertion tube control assembly of claim 12 wherein the elongated support has a distal end furthest from the handle and a transverse groove located near the distal end; and
   the fastening means comprises a spring loaded release slide having an aperture, the release slide being adapted to receive the end of the elongated support within the aperture and to releasably engage the transverse groove to secure the control knob assembly to the handle.

14. The endoscope insertion tube control assembly of claim 13 wherein the distal end of the support shaft forms a tapered head such that the tapered head causes the release slide to move to allow the head to be received by the slide release aperture and thereby allowing the release slide to releasably engage the transverse groove.

15. The endoscope insertion tube control assembly of claim 11, further comprising a clip positioned concentrically around the second control shaft so as to prevent detachment of the second brake plate from the second control shaft.

16. The endoscope insertion tube control assembly of claim 11 wherein the second control shaft includes a retaining ridge formed on its exterior, the insertion tube control assembly further comprising a plurality of shaft set screws extending transversely through the first control shaft, the set screws extending far enough into a space between the control shafts engage the retaining ridge a thereby stabilize axial movement between the control shafts when the control knob assembly is removed from the handle.

17. A method of attaching a control assembly is a unit to an endoscope having an insertion tube and a handle having a support shaft the control assembly including:
   a spring-loaded engagement member;
   a removable first controlling means for controlling up/down movement of the insertion tube;
   removable second controlling means for controlling left/right movement of the insertion tube;
   removable braking means for braking up/down and left/right movement of the insertion tube, the braking means being coupled to the controlling means such that the braking means and the controlling means are removable as a unit, the braking means including:
- a first braking mechanism, coupled to the first controlling means, for releasably restricting up/down movement of the insertion tube; and
- a first brake actuating means coupled to the first braking mechanism, for causing the first braking mechanism to restrict up/down movement of the insertion tube;
- a second braking mechanism, coupled to the second controlling means, for releasably restricting left/right movement of the insertion tube; and a second brake actuating means coupled to the second braking mechanism, for causing the second braking mechanism to restrict left/right movement of the insertion tube; the method comprising pushing the control assembly is a unit onto the support shaft of the endoscope handle, the pushing step causing the support shaft to force the engagement member to compress a spring that is loading the engagement member, and springing the engagement member of the control assembly into engagement with the support shaft.

18. The method of claim 17, further comprising detaching the control assembly as a unit from the endoscope handle by depressing a button coupled to the engagement member to disengage the engagement member from the shaft support and pulling the control assembly as a unit away from the endoscope handle.

* * * * *

UNITED STATES PATENT AND TRADEMARK OFFICE
CERTIFICATE OF CORRECTION

PATENT NO. : 5,329,887

DATED : July 19, 1994

INVENTOR(S) : Robert E. Ailinger and Robert J. Herrington

It is certified that error appears in the above-identified patent and that said Letters Patent is hereby corrected as shown below:

In column 10, claim 17, line 57, please delete "is" and substitute therefor --as--.

Signed and Sealed this

Eighth Day of November, 1994

Attest:

BRUCE LEHMAN

Attesting Officer

Commissioner of Patents and Trademarks